(12) United States Patent
Shpantzer

(10) Patent No.: US 7,426,035 B2
(45) Date of Patent: *Sep. 16, 2008

(54) SYSTEM AND METHOD FOR CHEMICAL SENSING USING TRACE GAS DETECTION

(75) Inventor: Isaac Shpantzer, Bethesda, MD (US)

(73) Assignee: CeLight, Inc., Silver Spring, MD (US)

( * ) Notice: Subject to any disclaimer, the term of this patent is extended or adjusted under 35 U.S.C. 154(b) by 63 days.

This patent is subject to a terminal disclaimer.

(21) Appl. No.: 11/561,966

(22) Filed: Nov. 21, 2006

(65) Prior Publication Data

US 2007/0115475 A1    May 24, 2007

Related U.S. Application Data

(63) Continuation-in-part of application No. 10/947,640, filed on Jan. 13, 2005, now Pat. No. 7,277,178, which is a continuation-in-part of application No. 10/669,130, filed on Sep. 22, 2003, now Pat. No. 7,327,913.

(60) Provisional application No. 60/739,179, filed on Nov. 23, 2005.

(51) Int. Cl.
  *G01B 9/02* (2006.01)
  *G01J 3/45* (2006.01)

(52) U.S. Cl. .................................................. 356/451

(58) Field of Classification Search ................ 356/128, 356/432, 451, 484, 517
See application file for complete search history.

(56) References Cited

U.S. PATENT DOCUMENTS

| | | | |
|---|---|---|---|
| 4,591,718 A | 5/1986 | Amer | |
| 4,790,664 A * | 12/1988 | Saito et al. | 356/432 |
| 4,830,502 A * | 5/1989 | Saito et al. | 356/432 |
| 5,060,312 A | 10/1991 | Delavaux | |
| 5,365,065 A | 11/1994 | Power | |
| 6,873,289 B2 | 7/2002 | Kwon | |
| 6,531,701 B2 | 3/2003 | Chou | |
| 6,709,857 B2 * | 3/2004 | Bachur, Jr. | 435/288.7 |
| 6,797,944 B2 | 9/2004 | Nguyen | |
| 7,277,178 B2 * | 10/2007 | Shpantzer et al. | 356/451 |
| 2001/0041366 A1 | 11/2001 | Lewis | |
| 2005/0207943 A1 | 9/2005 | Puzey | |

OTHER PUBLICATIONS

U.S. Appl. No. 10/669,130, filed May 20, 2004, Shpantzer.
U.S. Appl. No. 10/947,640, filed May 19, 2005, Shpantzer.
5. Bialkowski S. E. "Photothermal spectroscopy methods for chemical analysis", John Wiley & sons, USA, 1996, pp. 331-337.

* cited by examiner

Primary Examiner—Michael A Lyons

(57) ABSTRACT

A system and method is proposed for chemicals detection such as explosives and others, which are based on sensing of trace gases associated with the chemical. This sensing includes detection of spectrum and relative concentration of the trace gases followed by the chemical identification based on these data. The sensing is based on photothermal interferometry method modified by implementation of coherent optical detection. This modification essentially improves the device performance by increasing its sensitivity and selectivity. Improved characteristics of the device allow remote sensing of the interrogated chemicals at a distance up to 1000 meters, which is crucial for explosives detection. The coherent optical detection is performed by a coherent receiver based on 90-degrees optical hybrid.

20 Claims, 6 Drawing Sheets

(a)                                                        (b)

SYSTEM AND METHOD FOR CHEMICAL SENSING USING TRACE GAS DETECTION

CROSS-REFERENCE TO RELATED APPLICATIONS

The present invention is a continuation-in-part of the U.S. Ser. No. 10/669,130, filed Sep. 22, 2003, now U.S. Pat. No. 7,327,913 and U.S. Ser. No. 10/947,640, filed Jan. 13, 2005, now U.S. Pat. No. 7,277,178 all of which are fully incorporated herein by reference. This invention claims benefit of U.S. provisional patent application 60/739,179 filed Nov. 23, 2005.

FIELD OF INVENTION

This invention relates generally to the systems and methods for chemicals detection such as explosives and others, and more particularly to optical devices and the methods of their use based on sensing of trace gases associated with the chemical. This sensing includes detection of spectrum and relative concentration of the trace gases.

BACKGROUND OF THE INVENTION

Trace gas detection relies on vapors emitted from the explosive or on explosive particles that are deposited on nearby surfaces. Optical detection of explosives is a very challenging task because of complexity of optical spectra of detected materials and their low concentration. Method's sensitivity and selectivity are two main requirements for the detecting technology.

Nguyen et al., in U.S. Pat. No. 6,797,944, disclose a laser desorption and detection of explosives, narcotics and other chemical substances. The Nguyen et al. technique employs a compact scanning apparatus including an optical system to deliver a beam of pulsed infrared laser light that illuminates an interrogation area of the surface. The illumination described by Nguyen et al. is sufficiently intense and of such duration as to cause selective ablation of molecules of contraband substance present on a surface without substantially damaging the surface. A portion or sampling of the ablated molecules is collected and transferred to a separate chemical analysis system where a detector reacts to the sampled portion and activates an audible or visible alarm. A traceable residue of the detected contraband is left on the article for subsequent forensic analysis.

In U.S. Pat. No. 4,591,718 by Amer a sequence of infrared light pulses of progressively changing wavelengths is directed into an interrogated region and additional probe light beam is directed along the sample surface adjacent the region. Infrared wavelengths at which strong absorption occurs in the region are identified by detecting the resulting deflections of the probe beam caused by thermally induced index of refraction changes in the air or other medium adjacent the region.

Remote trace gas detection and analysis are disclosed in U.S. Pat. No. 6,531,701 by Chou. A beam of electromagnetic radiation is used to radiate a cloud and thermalize it by collisional energy transfer between the molecules that absorb the radiation. Emission from the cloud is resolved by a spectrometer.

It is well known that dogs are extremely sensitive to various smells. They have an ability to distinguish a particular explosive from a variety of other confusing smells. This unique selectivity combined with extremely high sensitivity (500 parts per trillion) make them exceptional helpers for security departments.

Most substances targeted for detection by working dogs (e.g., explosives and illicit drugs) are composed of many compounds. Dogs learn to use one constituent compound or combination of constituent compounds to recognize a particular substance. These compounds are called the dog's detection odor signature for that substance.

The present invention discloses an optical method for chemical detection based on trace gas detection similar to sniffing dog's odor signature detection manner.

Artificial olfactory methods were used in U.S. patent application No. 20010041366 by Lewis to detect trace level of analytes in patients' breath for determination of certain medical conditions.

Various optical methods have been developed to detect hidden explosives and other chemicals. The present invention discloses a system and method for remote chemicals detection using coherent detector based on opto-electronic device called 90-degrees optical hybrid. The details on coherent detector design and operating principle are unveiled in co-pending U.S. patent application Ser. No. 10/669,130, filed Sep. 22, 2003, all of which is fully incorporated herein by reference. Similar device is disclosed in U.S. Pat. No. 5,060,312 by Delavaux.

This invention claims benefit of co-pending U.S. patent application No. 20050105099 which discloses remote chemical sensing using photothermal interferometry with coherent detection of an optical signal. Standoff Explosive Detection Using Raman Induced Photothermal Interferometry provides safe identification of explosives at distances from 1 meters to 1000 meters with sensitivity as high as parts per billion. Detection time is less than one second. Low false alarm rates are achieved using multiple laser lines and fast processing algorithms. Principles of photothermal interferometry sensing are disclosed in U.S. Pat. No. 5,365,065 by Power and in Bialkowski S. E. "Photothermal spectroscopy methods for chemical analysis", John Wiley & sons, 1996, p. 331. None of these references disclose remote sensing, which is crucial for explosives detection. Remote sensing can only be achieved by implementation of modern integrated receivers as disclosed in U.S. patent application Ser. No. 10/669,130.

While the description of the present invention is focused on explosives detection, its use is not limited to this application. A wide variety of commercial applications are available including, but not limited to, environmental toxicology and remediation, biomedicine, such as microorganism classification or detection, material quality control, food and agricultural products monitoring, heavy industrial manufacturing, natural gas leakage detection, ambient air monitoring, worker protection, emissions control, and product quality testing.

SUMMARY OF THE INVENTION

The system and method are disclosed for chemicals detection (such as explosives and others) by optical beam detection technique. The chemical can be in a form of a gas or liquid or solid substance, or it can be dissolved in all of the above. The chemicals are at remote location from the detection system, preferably at a distance from 1 to 1000 meters.

The novelty of this invention is in ability to sense presence of an interrogated chemical by detection of trace gases signatures. Optical signature combines spectrum and concentration of the trace gas. This allows unveiling chemicals that are not detectable by direct spectroscopic methods due to complexity of their spectra.

Yet another novelty of this invention that this detection possesses extremely high sensitivity that allows detection at the remote location of the chemical under study, e.g. standoff location (outside of a blast range in case of explosives). This high sensitivity is provided by implementation of the coherent receiver of the optical signal.

The system comprises a strobe for excitation of trace gas molecules inside an interrogate volume and a probe unit, which can detect optical signatures of trace gases. In the preferred embodiment the probe unit includes a receiver that is balanced coherent optical detector combined with a digital signal processing (DSP) unit. The coherent optical detector is based on 90-degrees optical hybrid. DSP unit performs a processing of signals outputting the coherent optical detector.

In the preferred embodiment the strobe unit generates a set of light pulses, and the spectrum of this light is chosen as the most appropriate pattern to detect a particular chemical component, for example, trace gas of an explosive.

In the preferred embodiment the probe beam consists of coherent pulses, and the spectrum of this light is in near infrared, preferably 1.55 micrometer.

DETAILED DESCRIPTION OF THE PREFERRED EMBODIMENT

It is hard to overestimate the importance of development of reliable methods for explosives detection and diagnostics. Special attention is addressed to remote detection because of reduced risk factors. The present invention applies optical interferometric spectroscopy method and technique, which allows recognizing explosives remotely.

Table 1 shows trace gases and interfent gases for two types of explosives (TNT and RDX), however the present invention is not limited to these examples.

TABLE 1

Trace gases and interferent gases for TNT and RDX explosives.

| | Explosive substance | Trace gases | Interferent gases |
|---|---|---|---|
| 1 | TNT | DNT, DNB | Dodecane, toluene, acetone |
| 2 | RDX | Cyclohexanone, 2-ethyl-1-hexanol | Dodecane, acetone, toluene |

Figure 1:
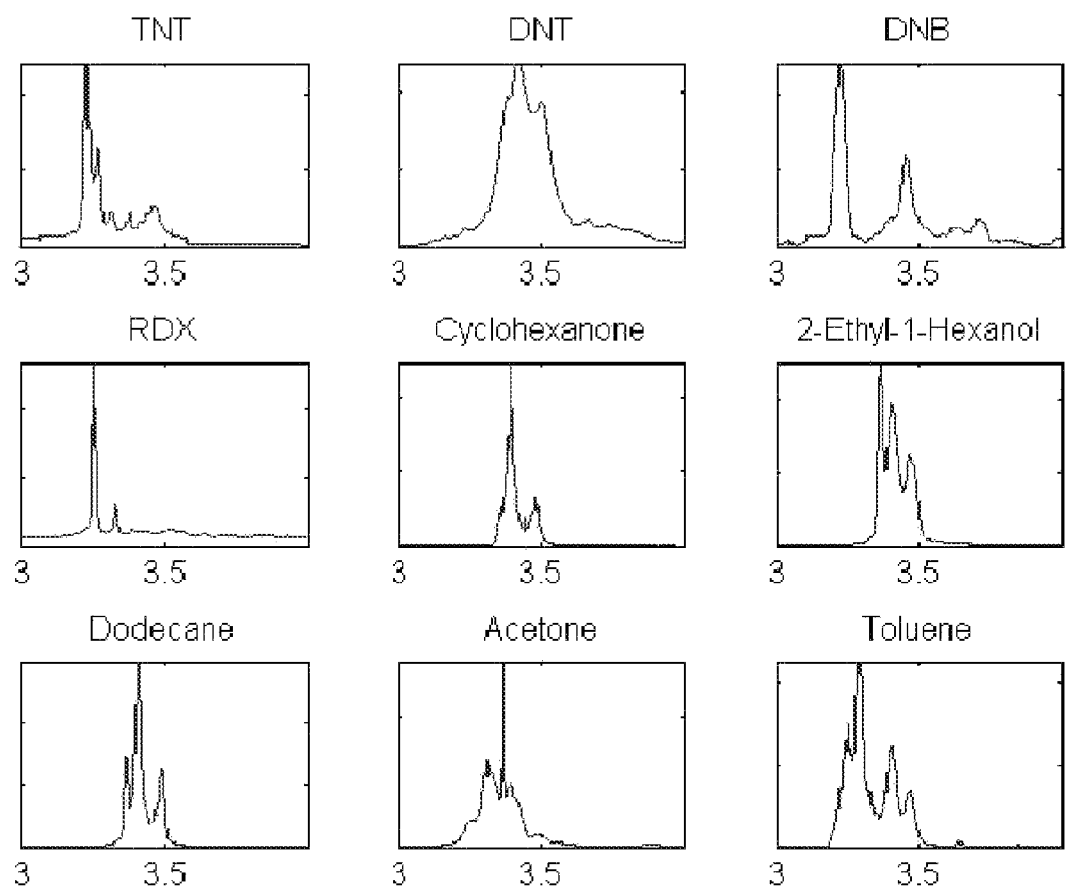
FIG. 1. Normalized optical spectra for some explosives, trace and intereferent gases.

Normalized optical spectra for these explosives, trace and intereferent gases are shown in FIG. 1. Complex mixed spectrum of real blast compound combines all spectra that correspond to these explosives, trace and intereferent gases with associated weights of each component. The weight is determined by the component's concentration.

Table 2 shows example relative concentrations (in ppb) of chemicals in air Volume surrounding the blast compositions.

TABLE 2

Relative concentration of chemicals in air volume surrounding the blast composition.

| | TNT | DNT | DNB | Dodecane | acetone | toluene |
|---|---|---|---|---|---|---|
| No. 1 | 0.03 | 0.72 | 0.24 | 0.5 | 0.5 | 0.5 |
| | RDX | Cyclo | 2-ethyl | Dodecane | acetone | toluene |
| No. 2 | 0.05 | 0.5 | 0.35 | 0.1 | 0.25 | 0.35 |

Multiple experiments demonstrated inability of modern technique to unveil the presence of explosives when the complex mixed spectrum is analyzed. In the present invention we disclose a method and system for separate detection of components of this complex mixed spectrum, so called optical signatures. Optical signature is a combination of spectral distribution and concentration for trace gases.

Figure 2:
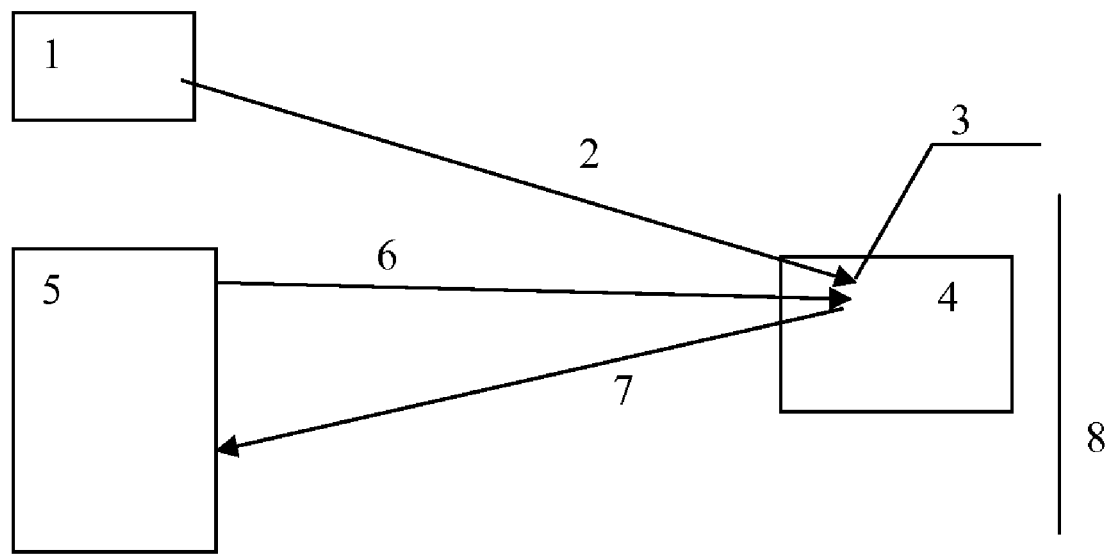
FIG. 2. Block diagram of the optical device for chemical detection based on the optical signature detection of the chemical component.

Optical signatures of trace gases may be measured by any technique. In the preferred embodiment, an optical device is used, the block diagram of which is shown in FIG. 2, where 1 is a strobe originating the first beam 2, illuminating an interrogated trace gas 3 inside a volume 4. The first beam 2 may be optionally focused on the particular spot inside the interrogated volume. A probe unit 5 irradiates a second beam 6 that experiences a phase change inside volume 4 due to the fact that the trace gas inside this volume is heated by absorption of the first beam 2. A third beam 7 is originated from the second beam 6 after its reflection or scattering from a surface 8 and incorporating changes occurred with the beam inside the volume 4. The probe unit 5 recovers information about the phase change in the beam 7 occurred in the volume 4.

A distance between the probe and the interrogated volume may be up to 1000 meters. A distance between the strobe and the interrogated volume also may be up to 1000 meters.

The strobe 1 is preferably a pulse light source operating in near or middle infrared range. The spectral range of the strobe is from 0.7 to 20 micrometers. Tunable Optical Parametric Oscillator laser produced by Photonics Industries, Inc. was used in our experiments. It operated in 2.2 to 3.4 micrometer range, which is in absorption band of many chemicals of interest. Strobe tunability allows changing the first beam wavelength in the way that it will coincide with the absorption spectrum of the interrogated trace gas. Radiation absorption by the trace gas causes heating and change of refractive index in the irradiated volume.

In one of the embodiments the strobe generates the beam 2 being monochromatic with the wavelength that falls in the absorption band of the trace gas. In another embodiment the strobe generates the beam 2 with a set of wavelengths that correspond to the peaks of the trace gas absorption spectrum.

In another embodiment the spectrum is an optical comb generator enable the programming and launching of very short pulses (pico-seconds) that are 'pre-shaped' in the frequency domain to go with the spectra of the trace gas. In the preferred embodiment the optical comb generator is an integrated $Li_2NbO_3$ optical device similar to the one disclosed in U.S. Pat. No. 7,123,800, having the same assignee as the present application, fully incorporated herein by reference. These pre-shaped pulses have their spectrum in near IR range.

They are converted by non-linear converter into mid IR range to match spectra of the trace gas.

Figure 3:
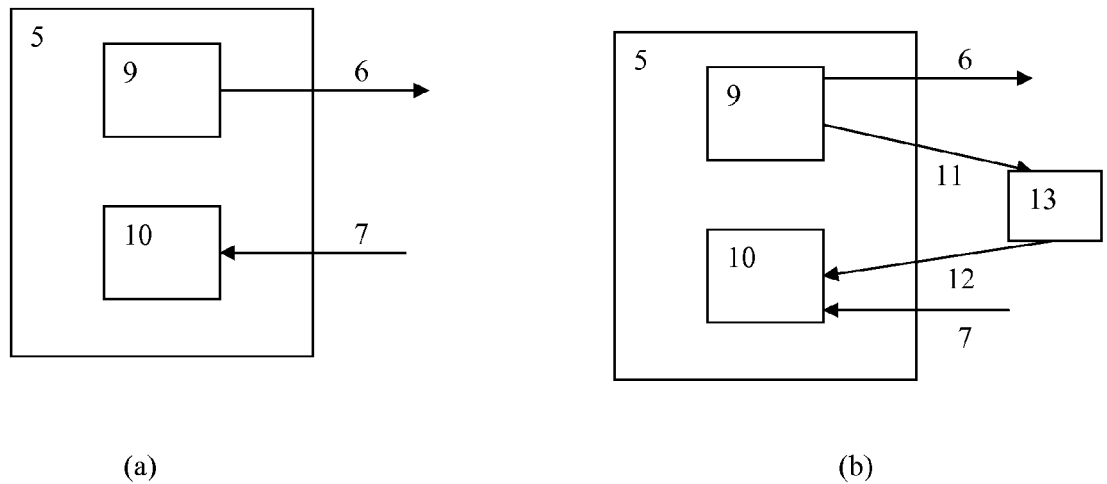
FIG. 3. Block diagram of the probe unit: (a) general schematics, (b) with local oscillator beam.

The probe unit 5 consists essentially of two parts: a transmitter 9 and a receiver 10 (FIG. 3), which may be located in one unit or may be separated by some distance in space. The transmitter and the receiver may be separated by some large distance in the range from 1 to 1000 meters.

The transmitter irradiates at least the optical beam 6, and the receiver receives at least the optical beam 7 (FIG. 3*a*). In the preferred embodiment the transmitter irradiates two beams: the optical beam 6 and an optical beam 11. The receiver 11 receives the optical beam 7 and an optical beam 12 as shown is FIG. 3*b*.

The optical beam 6 is a probe beam that passes through interrogated medium. The optical beam 11 forms a beam called local oscillator, which facilitates recovery of the information from the beam 6. The beam 11 passes through a reference path 13, incorporates some changes in phase and amplitude and enters the receiver 10 as the beam 12. The reference path is analogous to the path of the beam 6, however the beam 11 does not experience changes associated with the presence of heated interrogated chemical. For example, the reference path 13 can be the path from the probe unit 5 to the surface 8 and back, but outside the heated area of the trace gas in volume 4.

Figure 4:
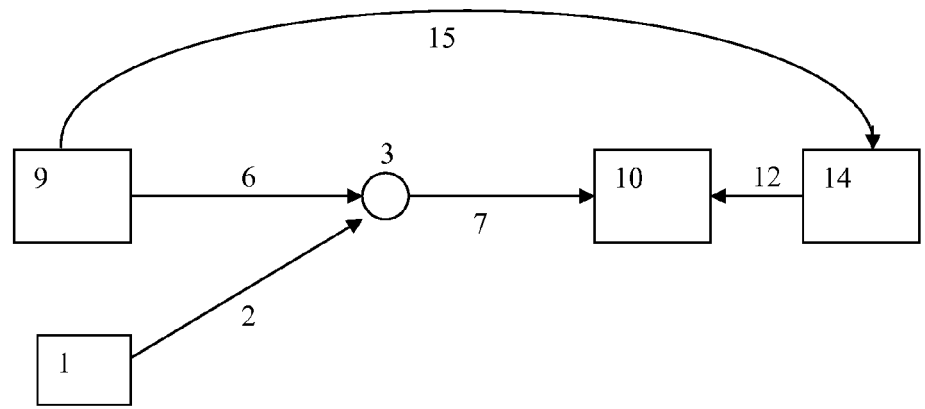
FIG. 4. Block diagram of the optical device for chemical detection operating in transmission mode. The transmitter and receiver are separated by some distance.

Alternatively a local oscillator beam 12 can be generated by a light source 14 being distinct from the transmitter and operating in-phase with the transmitter 9. In-phase operation is provided by a locking link 15. Block diagram of this alternative schematics that may operate in transmission mode is shown in FIG. 4.

Figure 5:
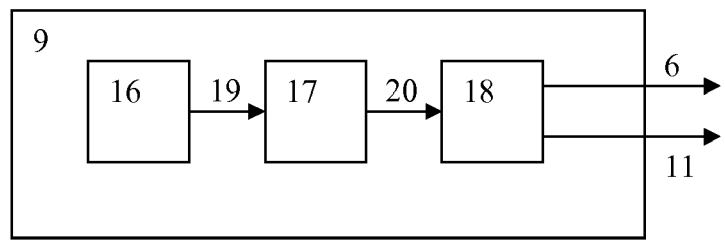
FIG. 5. Block diagram of the transmitter.

In the preferred embodiment the transmitter 9 is depicted in FIG. 5. It combines a light source 16, an optical modulator 17 and an optical beam splitter 18. Single frequency fiber laser produced by NP Photonics, Inc., AZ was used in our experiments as a light source. The modulator 17 and the splitter 18 are optional. MZ modulator and splitter produced by JDS Uniphase, CA can be used. The light source is preferably a laser with a wavelength in near infrared range from 0.7 to 2.0 micrometer. In the preferred embodiment the wavelength of the transmitter is around 1.55 micrometer. In another embodiment the wavelength of the transmitter is around 1.06 micrometer. The light source 16 irradiates a continuous optical beam 19, which is transformed into pulsed light beam by the modulator 17. An optical beam 20 that outputs by the modulator 17 is splitted into beams 6 and 11 by the splitter 18. The optical beam 6 serves as a probe beam that passes through the heated interrogated trace gas. The optical beam 11 serves as a local oscillator.

Figure 6:
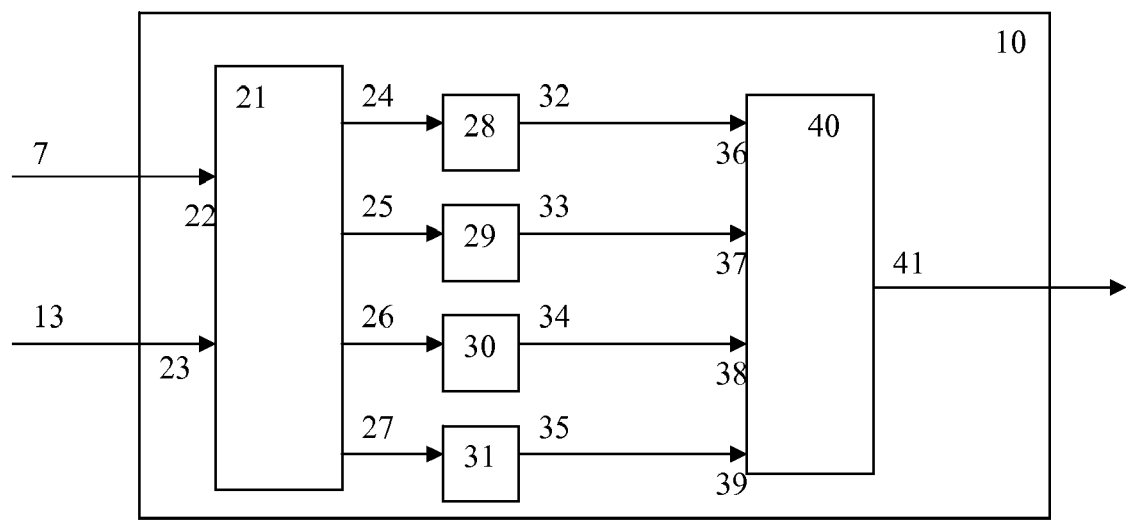
FIG. 6. Block diagram of the detector system for chemical detection.

The receiver 10 is shown in more details in FIG. 6. The receiver comprises electro-optical element 21 for mixing two input beams. The element 20 has two inputs (22 and 23) and four outputs 24, 25, 26, and 27. Photodetecting units 28, 29, 30 and 31 are connected to the outputs 24-27; they perform light conversion into electrical signals 32, 33, 34 and 35. In the preferred embodiment the photodetecting units 28-31 are balanced photodetectors combined with trans-impedance amplifiers (TIA). The electrical signals 32-35 impinge the inputs 36, 37, 38 and 39 of the DSP processing unit 40. The DSP unit performs the analysis and processing of the signals 32-35. The output signal 41 from the DSP unit 40 contains information on the probability of the presence/absence of the interrogated chemical and its concentration.

Digital signal processing may include compensation for air turbulence, Doppler shift in case the target is moving and vibrations of the target and the probe unit. It also may compensate homogeneities in reflection characteristic of the back surface 8.

Figure 7:
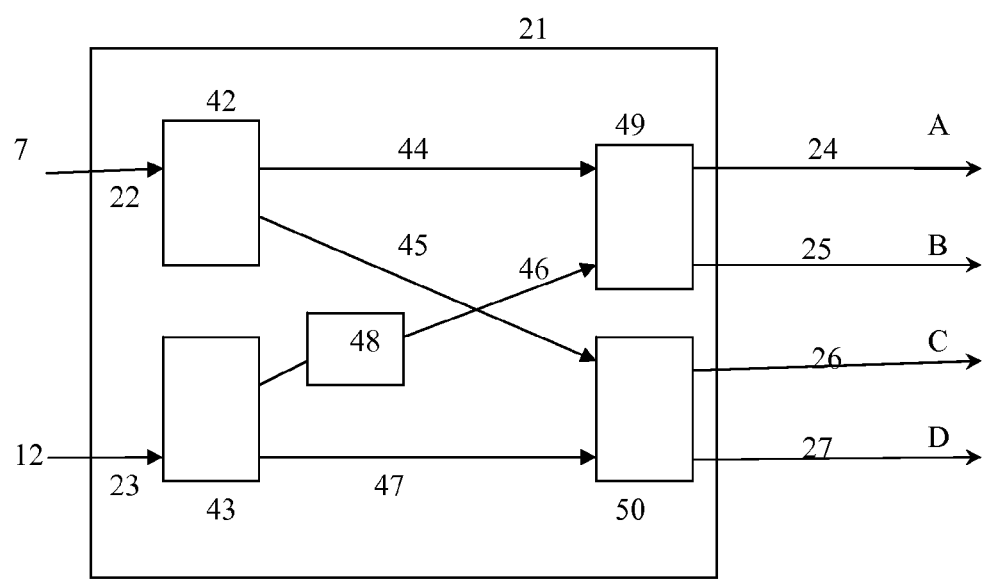
FIG. 7. 90-degrees optical hybrid being a part of the detector system of the present invention.

In the preferred embodiment the electro-optical element 21 is 90-degrees optical hybrid similar to the one disclosed in co-pending U.S. Patent application #20040096143 and in U.S. Pat. No. 5,060,312 by Delavaux both fully incorporated herein by reference. Coherent Optical Detector produced by CeLight, Inc., the assignee of the present invention, can be used for the coherent detection. The element 21 is shown in details in FIG. 7.

Two incoming optical signals 7 and 12, called, respectively, the signal S and the local oscillator L, impinge two inputs 22 and 23 of the optical hybrid 21. Passive couplers or splitters 42 and 43 divide the light coming from inputs 22 and 23 into four, preferably equal beams 44, 45, 46 and 47. The beam 46 passes through phase shifter 48 and gains the additional phase shift.

Beams 44 and 46 are mixed together by directional coupler 49. Beams 45 and 47 are mixed together, respectively, at the directional coupler 50. Couplers 49 and 50 intrinsically introduce the 90-degree phase shift between two outcoming signals. Bias voltages can be applied to each coupler 42, 43, 49 and 50 to set the 3 dB splitting operating point.

The resulting four output signals A, B, C, D, that come from outputs 24, 25, 26 and 27, can all have an adjustable relative phase difference with respect to each other. The first two outputs can provide the cosine of the relative phase between S and L after balanced detectors. The last two outputs can provide the sine of the relative phase.

If couplers 42, 43, 49 and 50 all are 3 dB couplers, and the phase shift 48 provides 90 degree phase shift, then all four outputs 24, 25, 26 and 27 have 90 degree relative phase difference of the form:

$$\{A=S+L, B=S-L, C=S+jL\ D=S-jL\}.$$

Optical detectors transfer optical signals A, B, C, and D into electrical signals, from which the information about the phase change in the beam 7, associated with the trace gas concentration, can be recovered.

In the preferred embodiment the coherent optical receiver is an integrated receiver as disclosed in co-pending U.S. Patent application #20040096143 by the same assignee incorporated herein by reference. As shown in '143 the recovery of the phase information encoded in the probe beam is an inherent property of the coherent detection.

The principle of the chemical spectrum and concentration revealing by photothermal spectroscopic interferometry are described in details in Bialkowski S. E. "Photothermal spectroscopy methods for chemical analysis", John Wiley & sons, 1996, p. 331-337. Sensitivity, signal-to-noise ratio and other parameters and details of photothermal spectroscopic interferometry method that implements 90-degrees optical hybrid as a part of detector are disclosed in co-pending U.S. patent application 20050105099 by the same assignee incorporated herein by reference. It is shown that the coherent optical receiver is able to sense the chemical in an amount of 1 part per trillion or more. The method and system unveiled in '099 disclose remote sensing technique which different from Bialkowski's approach.

Experiments carried out by the assignee demonstrated successful recognition of the interrogated blast compound by detection of optical signatures of trace gases. These results were not achieved by direct detection of the explosive compound as a whole.

Figure 8:
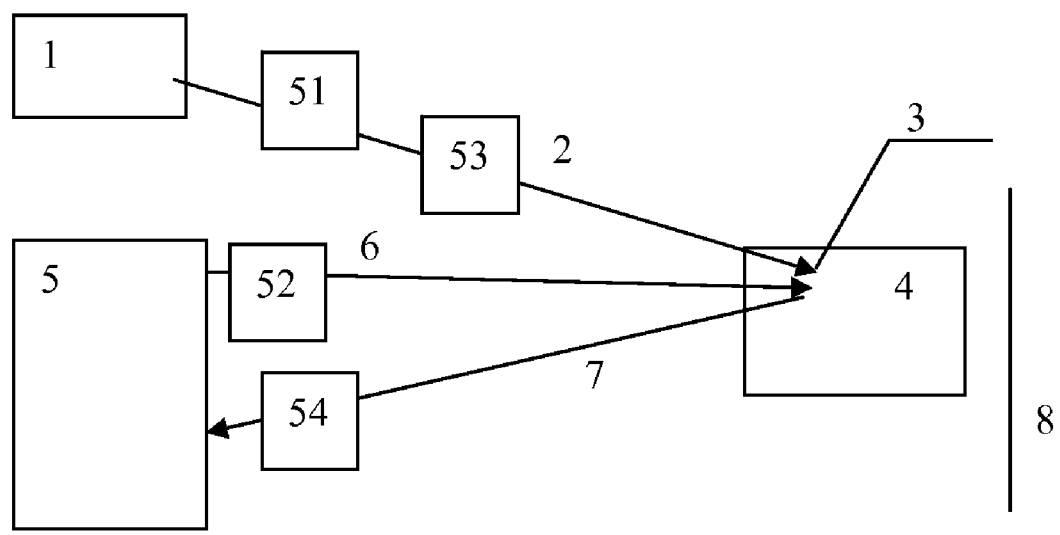
FIG. 8 Block diagram of the optical device for chemical detection with focusing and targeting units for the probe and the strobe beams.

The system depicted in FIG. 2 may optionally have targeting units 51 and 52 as shown in FIG. 8 for directing the beams 2 and 6 into the volume with interrogated chemical. The system may optionally have focusing unit 53 and 54 for focusing beam 6 and 7 on the interrogated trace gas volume and on the input of the probe unit 5 respectively. In one of the embodiments the targeting units 60 and 70 may be based on MEMs steering mechanism well known in the prior art, see for example U.S. Pat. No. 6,873,289 by Kwon.

The foregoing description of a preferred embodiment of the invention has been presented for purposes of illustration and description. It is not intended to be exhaustive or to limit the invention to the precise form disclosed, and obviously many modifications and variations are possible in the light of the above teaching. The described embodiment was chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A system for detecting a chemical, comprising:
   a strobe configured to irradiate a first beam with a spectral energy band across at least a portion of a characteristic absorption band of a trace gas associated with the chemical;
   a probe unit sending and receiving a probe beam, the probe unit configured to interferometrically sense and measure the absorption of the first beam by molecules of the trace gas by mixing the received probe beam with a local oscillator beam, coming from a local oscillator unit, and determine the trace gas concentration;
   a look-up table to identify what chemical corresponds to the determined trace gas;
   wherein the trace gas is at a remote location from the strobe and the probe unit.

2. The system of claim 1, wherein the probe unit comprises a coherent optical receiver.

3. The system of claim 2, wherein the coherent optical receiver is configured to sense the chemical in an amount of 1 part per trillion or more.

4. The optical system of claim 2, wherein the coherent optical receiver carries out homodyne detection of the probe beam.

5. The optical system of claim 2, wherein the coherent optical receiver includes an integrated 90-degrees optical hybrid.

6. The optical system of claim 2, wherein the coherent optical receiver is an integrated device.

7. The optical system of claim 2, wherein the transmitter and the coherent optical receiver are separated from each other by a distance of more than 1 meter.

8. The optical system of claim 2, wherein the coherent receiver is followed by a digital processing unit configured to determine the phase of the probe beam.

9. The system of claim 1, wherein the chemical identification is based on at least two types of the trace gases detected and their concentrations.

10. The system of claim 1, wherein remote detecting is performed at distance from 1 to 1000 meters from either the strobe or the probe unit.

11. The system of claim 1, wherein the chemical is in the form of a gas, liquid or solid.

12. The system of claim 1, wherein the chemical is at an explosive site, a site of pollution and a site of a chemical weapon.

13. The optical system of claim 1, wherein the first beam consists of coherent pulses.

14. The optical system of claim 1, wherein the strobe generates the first beam having a spectrum of wavelengths in the near and middle infrared range.

15. The optical system of claim 1, wherein the strobe generates the first beam having a spectrum of wavelengths from 2.5 to 4.5 micrometers.

16. The system of claim 1, wherein
   the first beam is configured to change a refractive index of the trace gas and
   the probe beam is configured to change a phase passing through the trace gas with the changed refractive index.

17. The optical system of claim 1, wherein the probe unit generates the probe beam consisting of coherent pulses.

18. The optical system of claim 1, wherein the probe unit generates the probe beam having a spectrum of wavelengths in the near infrared range.

19. The optical system of claim 1, wherein the probe unit generates the probe beam having a wavelength of about 1.55 micrometer.

20. A method for determining information about a chemical, comprising:
   directing a first beam to a remote location where a trace gas associated with the chemical is present,
   the first beam having one or more wavelengths that are in absorption band of a trace gas associated with the chemical, wherein the first beams interacts with the trace gas changing a refractive index of the trace gas;
   directing a probe beam to interact with the trace gas, receiving at least a portion of the probe beam at a receiver positioned remotely from the trace gas;
   mixing the received probe beam with a local oscillator beam producing interference and
   measuring a phase shift of the probe beam that is induced by the first beam and is indicative of at least one of, absorption spectrum and concentration of the trace gas;
   using a look-up table to identify the chemical basing on determined concentration of the trace gas.

* * * * *